United States Patent
Birnkrant (10) Patent No.: US 9,927,113 B2
(45) Date of Patent: Mar. 27, 2018

(54) HEAT SINK STRUCTURE AND LED HEAT SINK ASSEMBLIES

(71) Applicant: KARL STORZ Imaging, Inc., Goleta, CA (US)

(72) Inventor: Dashiell Birnkrant, Worcester, MA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 15/166,024

(22) Filed: May 26, 2016

(65) Prior Publication Data
US 2017/0343203 A1    Nov. 30, 2017

(51) Int. Cl.
| | |
|---|---|
| F21V 19/00 | (2006.01) |
| F21V 29/70 | (2015.01) |
| H01L 33/64 | (2010.01) |
| H01L 33/62 | (2010.01) |
| G02B 23/24 | (2006.01) |
| F21V 5/04 | (2006.01) |
| A61B 1/06 | (2006.01) |
| F21Y 101/02 | (2006.01) |

(52) U.S. Cl.
CPC ............ *F21V 29/70* (2015.01); *A61B 1/0684* (2013.01); *F21V 5/04* (2013.01); *F21V 19/0025* (2013.01); *G02B 23/2461* (2013.01); *H01L 33/62* (2013.01); *H01L 33/642* (2013.01); *H01L 33/647* (2013.01); *F21Y 2101/02* (2013.01)

(58) Field of Classification Search
USPC .................................................. 362/294, 382
See application file for complete search history.

(56) References Cited

U.S. PATENT DOCUMENTS

| | | | |
|---|---|---|---|
| 7,488,088 B2 | 2/2009 | Brukilacchio | |
| 8,602,971 B2 | 12/2013 | Farr | |
| 2003/0035048 A1 | 2/2003 | Shipp | |
| 2003/0218880 A1* | 11/2003 | Brukilacchio | A61N 5/062 362/293 |
| 2007/0191684 A1 | 8/2007 | Hirata | |
| 2009/0154166 A1 | 6/2009 | Zhang | |
| 2011/0306834 A1 | 12/2011 | Schrader | |
| 2013/0265798 A1 | 10/2013 | Kudo | |
| 2014/0240990 A1* | 8/2014 | Bae | F21V 29/22 362/294 |
| 2014/0275806 A1 | 9/2014 | Gunday | |
| 2014/0330081 A1 | 11/2014 | Shunichi | |
| 2016/0000309 A1 | 1/2016 | Weber | |

* cited by examiner

*Primary Examiner* — Matthew Mikels
(74) *Attorney, Agent, or Firm* — Michael Joseph Loi (57) ABSTRACT

A heat sink includes first and second elongated heat sink bodies. The first and second elongated heat sink bodies are each formed from a respective electrically and thermally conductive material and also each extend from an LED coupling end of the heat sink to a lead end of the heat sink. An electrical insulator material connects the first and second elongated heat sink bodies together so as to bodies are electrically isolated from each other. Each elongated heat sink body also includes a respective LED coupling surface at the LED coupling end of the heat sink and a respective lead connecting surface located on the respective body at a location spaced apart from the LED coupling end of the heat sink.

18 Claims, 5 Drawing Sheets

HEAT SINK STRUCTURE AND LED HEAT SINK ASSEMBLIES

TECHNICAL FIELD OF THE INVENTION

The invention relates to illumination systems for use in devices such as endoscopes. More particularly, the invention encompasses heat sinks, heat sink and LED assemblies, and devices incorporating such assemblies.

BACKGROUND OF THE INVENTION

Observation instruments such as endoscopes are used in medical and other applications to allow a visual inspection of locations which are not readily accessible. For example, endoscopes are used in medical applications to provide a view of an area within a patient's body. An endoscope typically includes an elongated shaft of relatively small diameter extending from a handle to a distal end. An imaging or viewing arrangement is included with the endoscope to allow a user to obtain a view from the distal end. This arrangement may include a system of lenses and a light conduit through the shaft to direct an image from the distal end to an eyepiece associated with the endoscope handle. Alternatively, the imaging or viewing arrangement may include an electronic imaging device at the distal end of the endoscope. Such an electronic imaging device collects image data and communicates that data through the shaft and handle ultimately to a processing system that assembles the data into an image displayed on a suitable display device. Whether the location at the distal end of the endoscope is viewed directly, or imaged electronically, the location must be illuminated sufficiently.

To provide the desired illumination, light may be generated by a light source at the endoscope handle and directed through suitable conduits in the shaft (such as optical fibers for example) to the endoscope distal end were the light can be directed as desired through suitable lenses. Alternatively to relying on light conducted through the shaft to the distal end of the endoscope, a suitable light source such as an LED lamp may be placed at the distal end of the endoscope to provide the required illumination. Although placement of a light source at the distal end of the endoscope provides a number of advantages, such an arrangement raises certain challenges. One challenge is that the light source and its associated electrical connections must remain small enough to fit in the distal end of the endoscope along with the objective lens for the imaging/viewing system and other elements which may be included at the distal end. Another challenge, particularly in medical applications, is that the light source must be capable of providing the desired illumination without heating the distal end of the endoscope beyond acceptable levels. Generally, the distal end of the endoscope must remain below 40° C. Thus any distal end light source must be capable of operating without releasing excessive heat to other elements within the distal end assembly.

Thermal management systems have been developed for addressing the issue of heat generated by illumination devices in endoscopes. U.S. Patent Application Publication No. 2011/0306834 discloses an endoscope with a heat pipe arranged to conduct heat away from a light source at the distal end of an endoscope. The arrangement shown in this prior publication includes a light source thermally coupled to two heat coupling elements which are in turn thermally coupled to the heat pipe. The heat pipe extends from the distal end of the endoscope to a heat sink at the opposite end of the shaft. Electrical power for the light source in U.S. Patent Application Publication No. 2011/0306834 is provided through wires which extend through the endoscope shaft alongside the heat pipe and heat coupling elements. While this prior system provides an arrangement for conducting heat away from a light source at a distal end of the endoscope, it does so at the cost of the added heat pipe taking up space within the shaft of the endoscope.

U.S. Patent Application Publication No. 2016/0000309 discloses an LED assembly in which an LED is mounted on a first conductor which is surrounded by a conductive sleeve. One electrical contact of the LED is coupled to the first conductor, while the other electrical contact of the LED is connected to the sleeve via a conductive tab. Both the first conductor and the conductive sleeve in this arrangement can dissipate waste heat from the LED. However, the sleeve required in the structure disclosed in U.S. Patent Publication No. 2016/0000309 increases the transverse dimension of the LED assembly, and also complicates manufacturing.

There remains a need for compact arrangements which can effectively conduct heat away from a light source mounted at the distal end of an observation instrument such as an endoscopic device.

SUMMARY OF THE INVENTION

It is an object of the invention to provide a heat sink particularly for use with a light source such as an LED mounted at the distal end of an optical scope. The invention also encompasses an LED and heat sink assembly as well as an observation instrument including such an LED and heat sink assembly.

A heat sink according to one aspect of the present invention includes first and second elongated heat sink bodies each defining a respective longitudinal axis and positioned substantially parallel to each other. The first and second elongated heat sink bodies are each formed from a respective electrically and thermally conductive material and also each extend from an LED coupling end of the heat sink to a lead end of the heat sink. An electrical insulator material connects the first and second elongated heat sink bodies together so as that bodies are electrically isolated from each other. Each elongated heat sink body also includes a respective LED coupling surface. A first LED coupling surface defines an end surface of the first elongated heat sink body at the LED coupling end of the heat sink, while a second LED coupling surface defines an end surface of the second elongated heat sink body at the LED coupling end of the heat sink. Each elongated heat sink body also includes a respective lead connecting surface located on the respective body at a location spaced apart from the LED coupling end of the heat sink.

The combination of the two substantially parallel elongated heat sink bodies of both thermally and electrically conductive material together with their electrical isolation and LED coupling surfaces according to this first aspect of the invention provides a number of advantages. One advantage is that the electrodes of an LED may be soldered or otherwise electrically connected directly to the elongated heat sink bodies. The elongated heat sink bodies may thus provide a power connection to the LED while simultaneously providing a good thermal conduction path to conduct heat away from the LED to electrically conductive leads which may be soldered or otherwise electrically connected to the respective lead connecting surfaces. Another advantage of the heat sink arrangement according to this first aspect of the invention is that the elongated heat sink bodies may be arranged to provide a very compact transverse shape. Thus the heat sink makes very efficient use of the limited space within the optical scope distal end.

According to another aspect of the invention, an LED and heat sink assembly includes an LED having a light emitting side and a contact side. The contact side is opposite to the light emitting side and includes an anode and a cathode located at spaced apart positions. A first elongated heat sink body defines a first longitudinal axis extending transverse to the contact side of the LED, and has an LED coupling surface at one end in electrical contact with the anode of the LED. A second elongated heat sink body defines a second longitudinal axis also extending transverse to the contact side of the LED, and has an LED coupling surface at one end in electrical contact with the cathode of the LED. Both of the first and second elongated heat sink bodies are formed from a respective electrically and thermally conductive material and the two bodies are connected together by an electrical insulator material so that the two heat sink bodies are electrically isolated from each other along their length. Each elongated heat sink body includes a respective lead connecting surface located on the respective body at a location spaced apart from the LED, and preferably at the end opposite to that connected to the LED.

The LED and heat sink assembly according to this second aspect of the invention is well adapted for use in small assemblies such as those making up the distal end of an optical scope. In particular, the distal end of an optical scope may include a sleeve having openings defined therein for receiving the various components of the distal end assembly. In this arrangement, the LED and heat sink assembly according to this second aspect of the invention may be inserted LED end first into an opening reserved for the LED and retained in place by a suitable method.

According to another aspect of the invention, an LED and heat sink assembly according to the second aspect described above is combined with an observation instrument including a handle and shaft. The LED and heat sink assembly is mounted in the observation instrument so that the LED resides at a distal end of the shaft with the light emitting side of the LED facing outwardly.

In one implementation of a heat sink or heat sink assembly according to any of the foregoing aspects of the invention, the two elongated heat sink bodies each include a respective planar longitudinal face in contact with the electrical insulator material. Regardless of the shape of the connected surfaces of the two heat sink bodies, the electrical insulator material may comprise an epoxy material or any other suitable bonding and electrical insulating material.

The elongated heat sink bodies may have an external shape which allows the heat sink arrangement to be readily mounted in an assembly. This is particularly helpful in implementations in which the heat sink is incorporated in a compact device such as the distal end of an endoscope. In one preferred implementation, each elongated heat sink body includes a curved outer surface so that the two bodies together form a portion of a cylindrical shape.

In implementations of a heat sink or heat sink assembly according to any of the foregoing aspects of the invention, the lead connecting surface of each heat sink body may comprise a feature that facilitates the connection of a conductor for supplying electrical power to the LED. One such feature may comprise a hole drilled or otherwise formed in the end of the respective heat sink body opposite the end coupled (or to be coupled) to the LED. Regardless of whether such a connection facilitating surface is provided as the lead surface of the elongated heat sink body, the power supplying conductor may be soldered to the lead connecting surface or connected in any other way that provides a good electrical and thermal interface between the conductor and the heat sink body. Similarly, the electrodes of the LED at the opposite end of the heat sink structure may be soldered to the respective LED coupling surface or positioned in any other way to provide a good electrical and thermal interface between the respective LED electrode and the respective LED coupling surface.

It should be noted that although certain implementations of the present invention are described with reference to endoscopes, the invention is certainly not limited to applications in endoscopes. Rather, in implementations according to any of the foregoing aspects of the invention, the observation device in which the heat sink may be employed may be an optical scope such as an endoscope, exoscope, or borescope.

These and other advantages and features of the invention will be apparent from the following description of representative embodiments, considered along with the accompanying drawings.

DESCRIPTION OF REPRESENTATIVE EMBODIMENTS

Heat sinks and heat sink assemblies within the scope of the present invention will be described below primarily with reference to applications in an endoscope. This reference to an endoscope is intended merely as a representative example application and is not intended to be limiting. Implementations include other observation instruments including optical scopes such as exoscopes and borescopes in addition to endoscopes.

Figure 1:
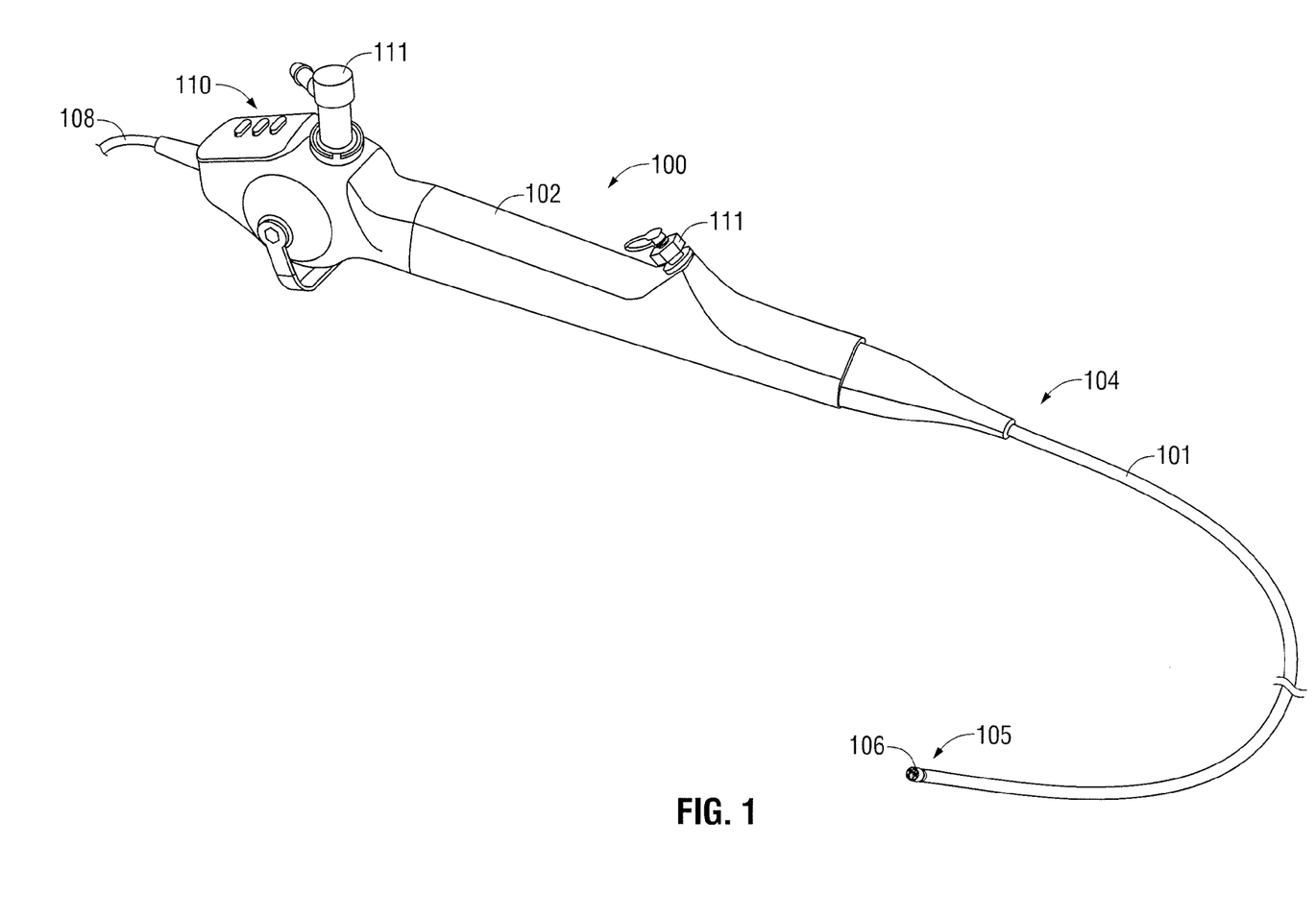
FIG. 1 is a view in perspective of an endoscope including an LED and heat sink assembly according to an embodiment of the present invention.

Referring to FIG. 1, an endoscope 100 employing an LED and heat sink assembly according to one aspect of the present invention includes an elongated shaft 101 and a handle 102. Shaft 101 extends from a proximal end shown generally at reference numeral 104 connected to handle 102 to a distal end generally indicated at reference numeral 105. A distal end assembly 106 is included at the shaft distal end 105 and includes one or more LED and heat sink assemblies according to an aspect of the present invention. The LEDs and other features of distal end assembly 106 are not shown in FIG. 1 due to the scale of the figure but will be described in detail below, particularly with reference to FIGS. 2-6.

Endoscope 100 receives electrical operating power through a cable 108 which extends from a proximal end of handle 102 in this example endoscope. This power may be used to operate the LED or LEDs associated with distal end assembly 106 and other electronic elements associated with the distal end assembly, such as an imaging device which may be located in that assembly. Also, data signals from such an imaging device may be communicated through appropriate conduits within shaft 101 and handle 102 to cable 108. These data signals may be communicated through cable 108 to processing equipment (not shown) which processes the image data and drives one or more video monitors to display the images collected at distal end assembly 106. Those familiar with endoscopic systems will appreciate that endoscope 100 includes a number of features such as controls 110 for controlling the operation of the endoscope and ports 111 for introducing fluids or applying a suction to a working channel included in the endoscope. These additional features and the general operation and control of endoscope 100 will not be described further herein in order to avoid obscuring the present invention in unnecessary detail.

Figure 2:
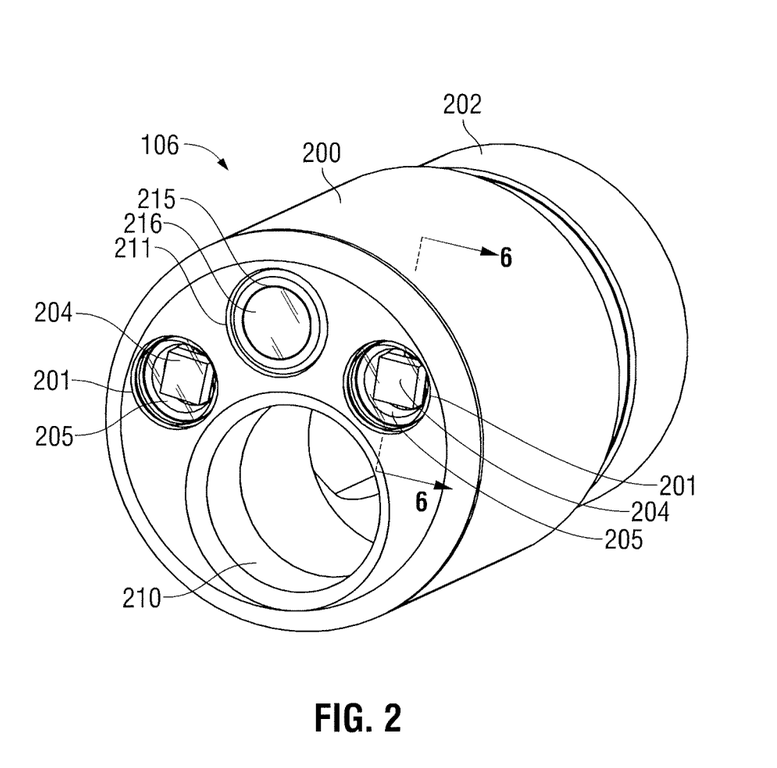
FIG. 2 is a front perspective view of the assembly at the distal end of the endoscope shown in FIG. 1.
Figure 3:
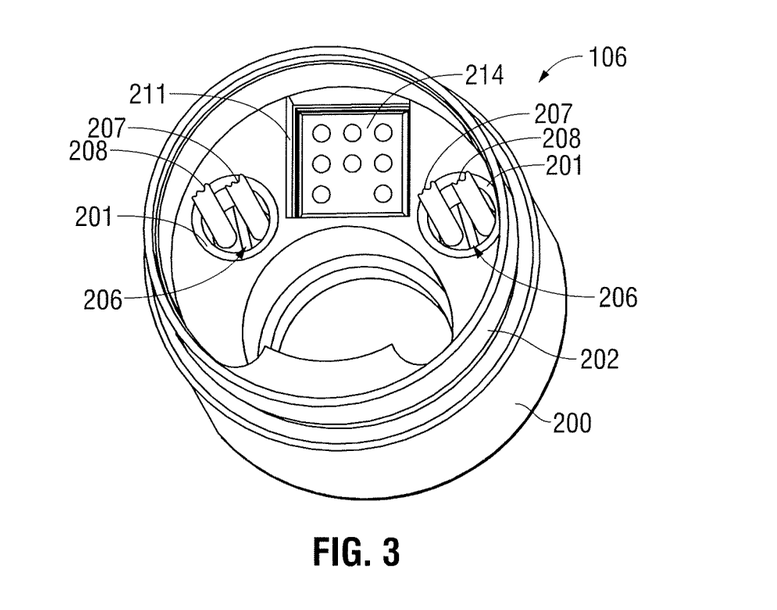
FIG. 3 is a rear perspective view of the assembly shown in FIG. 2.

FIGS. 2 and 3 show distal end assembly 106 separated from shaft 101 shown in FIG. 1. In this representative embodiment, distal end assembly 106 includes a sleeve 200 having a front end shown in the perspective of FIG. 2 and a base end shown in the perspective of FIG. 3. The base end of sleeve 200 is shown in FIG. 3 as including a shaft connecting feature 202 which can be inserted into a tube comprising the endoscope shaft (101 in FIG. 1). Sleeve 200 includes two separate LED assembly receiving openings 201 which are each adapted to receive a respective LED and heat sink assembly according to an aspect of the present invention. In the view of FIG. 2 only the LED 204 of the LED and heat sink assembly is visible through transparent cover or lens 205. In the view of FIG. 3 only the heat sink inner end (shown generally at reference numeral 206) is visible along with power supply wires 207 and 208 leading to the heat sink. Further details regarding the placement of the LED and heat sink assemblies within sleeve 200 will be described below with reference to FIG. 6.

Sleeve 200 also includes a working channel opening 210 and an imaging assembly opening 211. In this example the imaging assembly includes a CMOS imaging device 214, the back of which is visible in the view of FIG. 3, and a lens assembly 215, the outermost part of which is visible in FIG. 2 behind transparent protective cover 216. Working channel opening 210 may receive the end of a tube which represents a working channel for performing various functions through distal end assembly 106. In particular, the working channel may be used to apply suction or apply a fluid through the endoscope, or receive a tool which may be operated through the endoscope.

Figure 4:
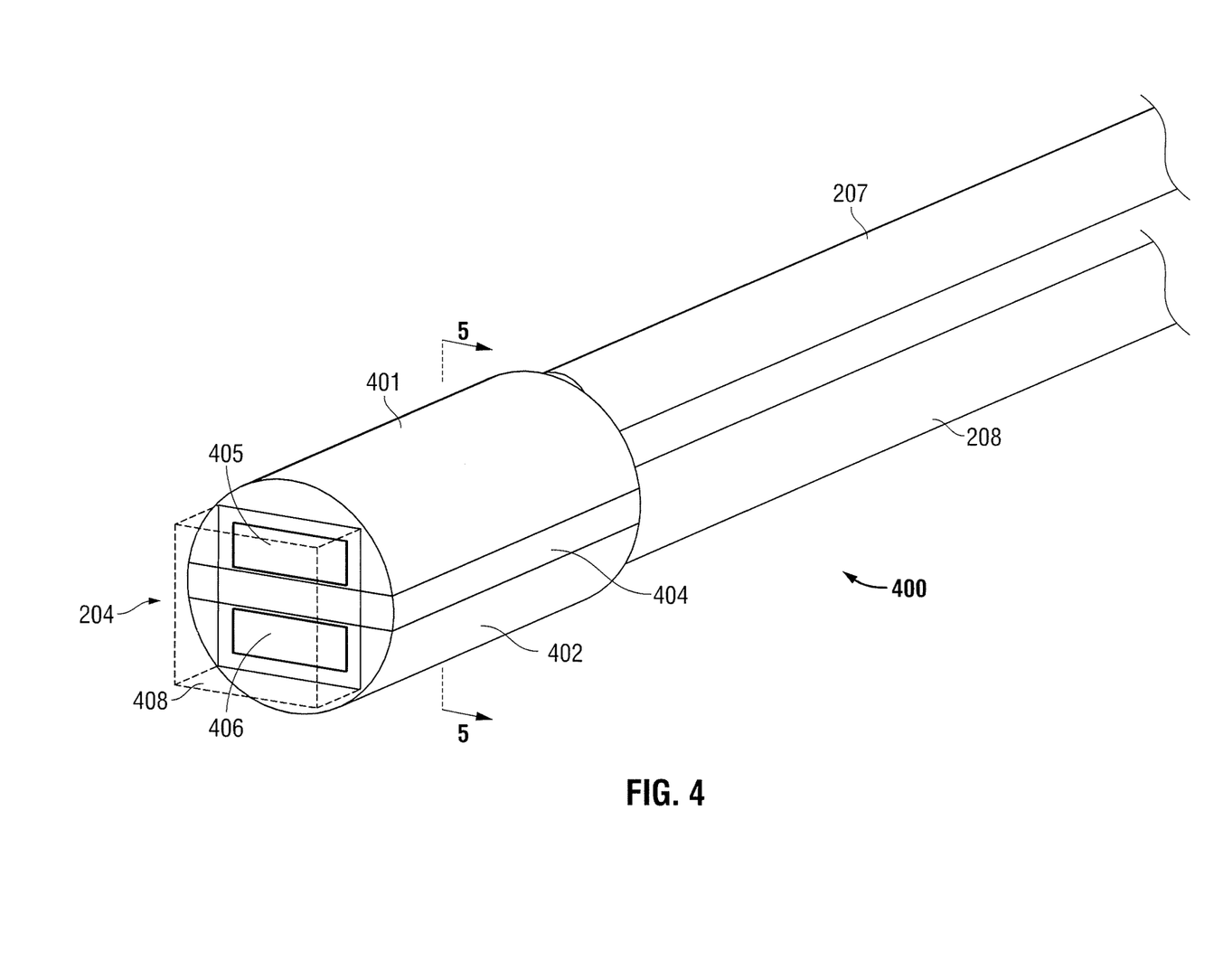
FIG. 4 is a view in perspective of an LED and heat sink assembly which may be used in the endoscope distal end assembly shown in FIGS. 2 and 3.
Figure 5:
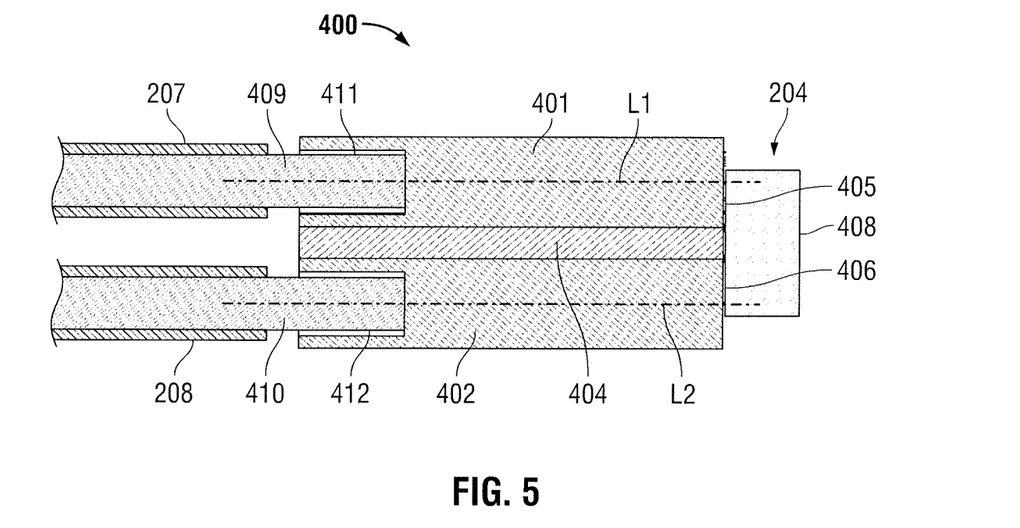
FIG. 5 is a view in section taken along line 5-5 in FIG. 4.

FIGS. 4 and 5 show one of the LED and heat sink assemblies from sleeve 200 in FIGS. 2 and 3. This LED and heat sink assembly 400 includes LED 204 and a heat sink which is made up of a first elongated heat sink body 401 and a second elongated heat sink body 402 separated by a layer of electrically insulating material 404. First heat sink body 401 has a longitudinal axis L1 that extends essentially parallel to a longitudinal axis L2 of second heat sink body 402 (the longitudinal axes L1 and L2 being shown in FIG. 5). LED 204 is mounted at a first end of the heat sink and is shown in dashed lines in FIG. 4 so that its electrical contact pads (405 and 406 respectively) are visible in that view. It will be appreciated that these contact pads 405 and 406 are formed on a back (contact) surface of LED 204 opposite a light emitting side 408. Pad 405 is electrically coupled to an LED coupling surface of elongated heat sink body 401 at the first end of the heat sink, while pad 406 is electrically coupled to an LED coupling surface of elongated heat sink body 402 at that end of the heat sink. At the opposite end of the heat sink, heat sink bodies 401 and 402 are each electrically coupled to a conductor, 409 and 410, respectively, of power supply wires 208 and 209. In this arrangement a suitable LED driving signal applied across conductors 409 and 410 causes LED 204 to emit the desired light.

LED 204 may be coupled to each elongated heat sink body 401 and 402 by any suitable arrangement that provides the required electrical and thermal connection. Preferred implementations may simply solder each LED contact pad 405 and 406 to a respective planar surface which makes up the LED coupling surface of the respective heat sink body. The opposite end of each elongated heat sink body 401 and 402 comprises a lead connection surface which in this case includes a recess or hole 411 and 412, respectively, formed in the respective body for receiving an end of one of the power supply conductors 409 and 410. The conductors 409 and 410 may be soldered in place in this arrangement to provide the desired robust connection with good electrical and thermal conduction between each heat sink body 401 and 402 and the respective conductor.

Figure 6:
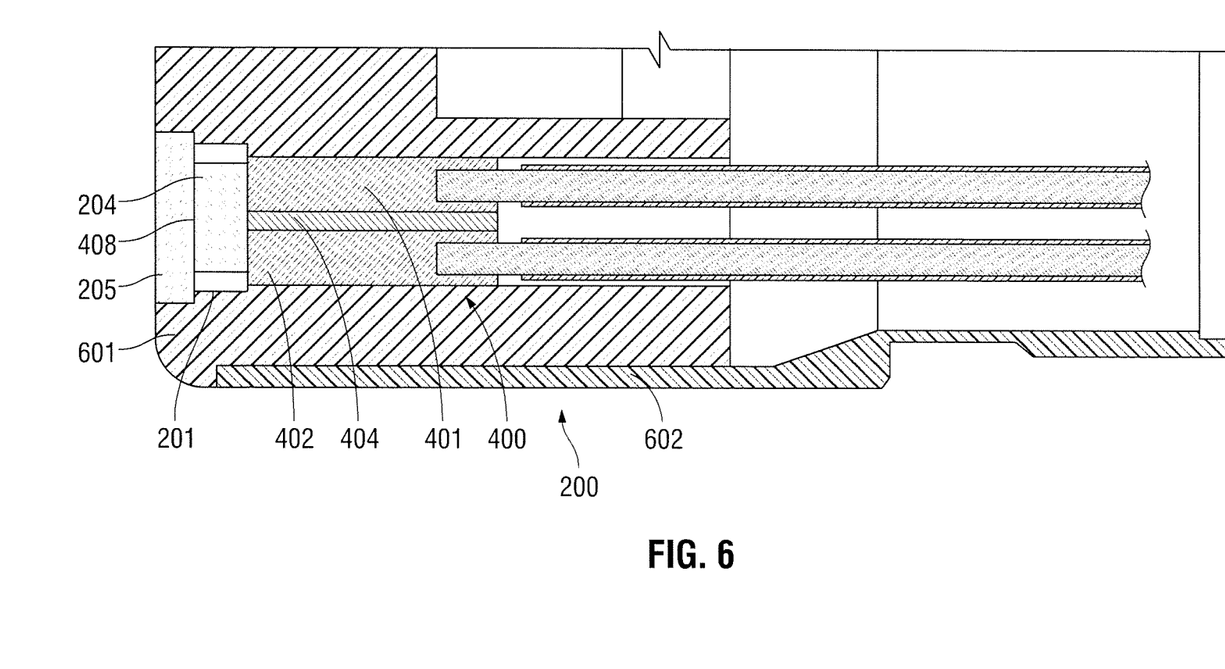
FIG. 6 is a view in section taken along line 6-6 in FIG. 2.

The section view of FIG. 6 shows heat sink assembly 400 mounted in an operating position within sleeve 200. In this embodiment, sleeve 200 is made up of an end part 601 and an intermediate part 602. LED receiving opening 201 is located in end part 601. The protective cover/lens 205 is mounted at the distal end of LED assembly receiving opening 201 (the leftmost end in the orientation of the figure). In this example, LED and heat sink assembly 400 is placed in the receiving opening 201 with LED 204 having its light emitting side 408 facing and adjacent to cover/lens 205.

It should be noted that the sleeve end part 601 shown in FIG. 6 is formed from an electrically non-conductive material. Thus the outer surfaces of the two heat sink bodies 401 and 402 require no cover material and may contact the surfaces of opening 201. If desired, and certainly where the structure (such as end part 601) receiving the LED and heat sink assembly is made from an electrically conductive material, an electrically nonconductive sheath (not shown) may be provided over the heat sink so as to separate the two elongated heat sink bodies 401 and 402 from the receiving structure, and maintain electrical isolation between the two heat sink bodies.

The cylindrical shape of the heat sink made up of bodies 401 and 402 together with insulating layer 404 is preferred because it can be received in a corresponding cylindrically shaped opening in a sleeve such as sleeve 200 (shown in FIGS. 2, 3, and 6). This cylindrical heat sink and receiving opening make efficient use of the area available in the distal end assembly 106 (FIGS. 2 and 3). However, the invention is certainly not limited to this cylindrical shape.

Figure 7:
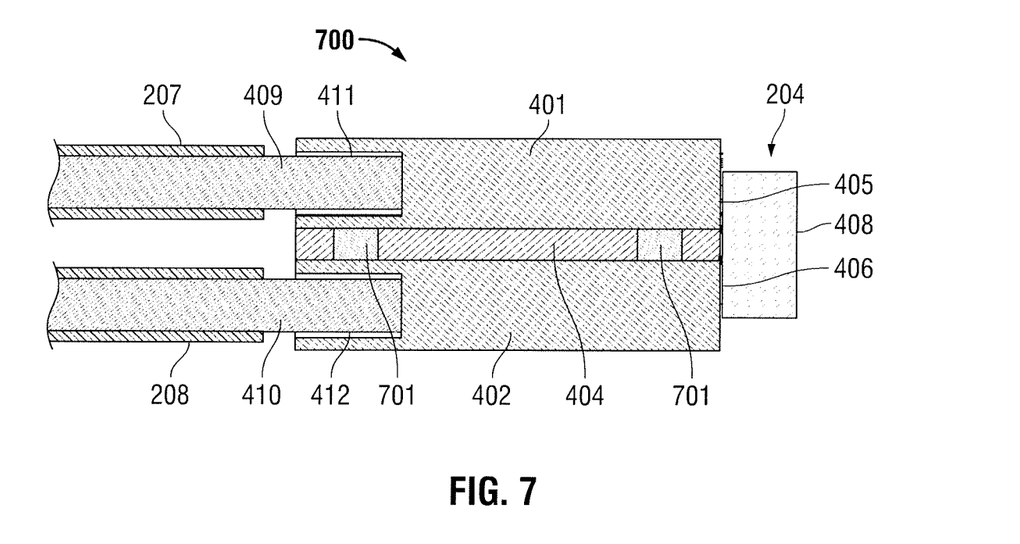
FIG. 7 is a view in section similar to FIG. 5, but showing an embodiment in which shims remain in the heat sink.

FIG. 7 shows a section view of an alternate embodiment of an LED and heat sink assembly 700 according to the present invention. This embodiment is identical to the example shown in FIGS. 4 and 5 except that FIG. 7 shows nonconductive shims 701 located between the two elongated heat sink bodies 401 and 402. Shims 701 may be left over from a manufacturing process for the heat sink assembly 700.

In the embodiments shown in FIGS. 4-7 each elongated heat sink body 401 and 402 may comprise a block of copper or aluminum or any other suitable material that exhibits both good thermal and electrical conductivity. The insulating material 404 may be any suitable material that maintains electrical isolation between the two heat sink bodies 401 and 402 (at the relatively low voltage which may be applied as the LED driving signal) and bonds the two bodies together. For example, insulating material 404 may comprise a high temperature epoxy.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. A heat sink for LEDs, the heat sink including:
   (a) a first elongated heat sink body defining a first longitudinal axis;
   (b) a second elongated heat sink body defining a second longitudinal axis extending substantially parallel to the first longitudinal axis, the first and second heat sink elongated sink bodies each being formed from a respective electrically and thermally conductive material, and each extending from an LED coupling end of the heat sink to a lead end of the heat sink;
   (c) an electrical insulator material connecting the first elongated heat sink body and the second elongated heat sink body together so as to electrically isolate the first elongated heat sink body from the second elongated heat sink body;
   (d) a first LED coupling surface defining an end surface of the first elongated heat sink body at the LED coupling end of the heat sink;
   (e) a second LED coupling surface defining an end surface of the second elongated heat sink body at the LED coupling end of the heat sink;
   (f) a first lead connecting surface located on the first elongated heat sink body at a location spaced apart from the LED coupling end of the heat sink along the first longitudinal axis; and
   (g) a second lead connecting surface located on the second elongated heat sink body at a location spaced apart from the LED coupling end of the heat sink along the second longitudinal axis.

2. The heat sink of claim 1 wherein the first and second elongated heat sink body each includes a respective planar longitudinal face in contact with the electrical insulator material.

3. The heat sink of claim 1 wherein the electrical insulator material comprises an epoxy material.

4. The heat sink of claim 1 wherein the first and second elongated heat sink body each include a curved outer surface so that the heat sink forms a cylindrical shape.

5. The heat sink of claim 1 wherein:
   (a) the first lead connecting surface comprises a first hole formed in the first elongated heat sink body at a second end of the heat sink opposite the LED coupling end of the heat sink; and
   (b) the second lead connecting surface comprises a second hole formed in the second elongated heat sink body at the second end of the heat sink.

6. An LED and heat sink assembly including:
   (a) an LED having a light emitting side and a contact side opposite the light emitting side, an anode and a cathode being located at spaced apart positions on the contact side;
   (b) a first elongated heat sink body having a first LED coupling surface in electrical contact with the anode of the LED, the first elongated heat sink body defining a first longitudinal axis extending transverse to the contact side of the LED;
   (c) a second elongated heat sink body having a second LED coupling surface in electrical contact with the cathode of the LED, the second elongated heat sink body defining a second longitudinal axis extending transverse to the contact side of the LED, the first and second elongated heat sink bodies each being formed from a respective electrically and thermally conductive material;
   (d) an electrical insulator material connecting the first elongated heat sink body and the second elongated heat sink body together so as to electrically isolate the first elongated heat sink body from the second elongated heat sink body;
   (e) a first lead connecting surface located on the first elongated heat sink body at a location spaced apart from the LED; and
   (f) a second lead connecting surface located on the second elongated heat sink body at a location spaced apart from the LED.

7. The LED and heat sink assembly of claim 6 wherein:
  (a) the first LED coupling surface is soldered to the anode of the LED to provide the electrical contact between the first LED coupling surface and the anode of the LED; and
  (b) the second LED coupling surface is soldered to the cathode of the LED to provide the electrical contact between the second LED coupling surface and the cathode of the LED.

8. The LED and heat sink assembly of claim 6 wherein the first and second elongated heat sink body each includes a respective planar longitudinal face in contact with the electrical insulator material.

9. The LED and heat sink assembly of claim 6 wherein the electrical insulator material comprises an epoxy material.

10. The LED and heat sink assembly of claim 6 wherein the first and second elongated heat sink body each include a curved outer surface so that the first and second elongated heat sink bodies together form a portion of a cylindrical shape.

11. The LED and heat sink assembly of claim 6 wherein:
  (a) the first lead connecting surface comprises a first hole formed in the first elongated heat sink body at an end of the elongated first heat sink body opposite to the first LED coupling surface; and
  (b) the second lead connecting surface comprises a second hole formed in the second elongated heat sink body at an end of the second elongated heat sink body opposite to the second LED coupling surface.

12. An observation instrument including:
  (a) a handle and shaft;
  (b) an LED mounted at a distal end of the shaft, the LED having a light emitting side and having a contact side opposite the light emitting side, an anode and a cathode being located at spaced apart locations on the contact side;
  (c) a first elongated heat sink body having a first LED coupling surface defining an end surface of the first elongated heat sink body in electrical contact with the anode of the LED, the first elongated heat sink body defining a first longitudinal axis extending transverse to the contact side of the LED;
  (d) a second elongated heat sink body having a second LED coupling surface defining an end surface of the second elongated heat sink body in electrical contact with the cathode of the LED, the second elongated heat sink body defining a second longitudinal axis extending transverse to the contact side of the LED, the first and second elongated heat sink bodies each being formed from a respective electrically and thermally conductive material;
  (e) an electrical insulator material connecting the first elongated heat sink body and the second elongated heat sink body together so as to electrically isolate the first elongated heat sink body from the second elongated heat sink body;
  (f) a first lead connecting surface located on the first elongated heat sink body at a location spaced apart from the first LED coupling surface; and
  (g) a second lead connecting surface located on the second elongated heat sink body at a location spaced apart from the second LED coupling surface.

13. The observation instrument of claim 12 wherein:
  (a) the first LED coupling surface is soldered to the anode of the LED to provide the electrical contact between the first LED coupling surface and the anode of the LED; and
  (b) the second LED coupling surface is soldered to the cathode of the LED to provide the electrical contact between the second LED coupling surface and the cathode of the LED.

14. The observation instrument of claim 12 wherein the first and second elongated heat sink body each includes a respective planar longitudinal face in contact with the electrical insulator material.

15. The observation instrument of claim 12 wherein the electrical insulator material comprises an epoxy material.

16. The observation instrument of claim 12 wherein the first and second elongated heat sink body each include a curved outer surface forming a portion of a cylindrical shape.

17. The observation instrument of claim 12 wherein:
  (a) the first lead connecting surface comprises a first hole formed in the first elongated heat sink body at a second end of the first elongated heat sink body opposite the first LED coupling surface; and
  (b) the second lead connecting surface comprises a second hole formed in the second elongated heat sink body at a second end of the second elongated heat sink body opposite the second LED coupling surface.

18. The observation instrument of claim 12 wherein the observation instrument is selected from a group consisting of an endoscope, an exoscope, and a borescope.

\* \* \* \* \*